United States Patent [19]

Gang

[11] Patent Number: 4,766,078
[45] Date of Patent: Aug. 23, 1988

[54] AUTOMATED CONSECUTIVE REACTION ANALYZER

[76] Inventor: Henry Gang, 42 Leighton Ave., Yonkers, N.Y. 10705

[21] Appl. No.: 709,657

[22] Filed: Mar. 7, 1985

[51] Int. Cl.$^4$ .................... G01N 21/13; C12M 1/34
[52] U.S. Cl. .................................. 435/291; 435/312; 422/64; 422/73; 436/43
[58] Field of Search .................. 435/291, 312; 422/68, 422/64, 67, 73; 436/43, 66, 70

[56] References Cited

U.S. PATENT DOCUMENTS

| | | | |
|---|---|---|---|
| 4,234,540 | 11/1980 | Ginsberg et al. | 422/64 |
| 4,260,580 | 4/1981 | Sindo et al. | 422/64 |
| 4,311,394 | 1/1982 | Manabe | 422/64 X |
| 4,313,735 | 2/1982 | Yamashita et al. | 422/64 X |
| 4,315,891 | 2/1982 | Sakurada | 422/64 |
| 4,344,768 | 8/1982 | Parker et al. | 422/64 X |
| 4,406,547 | 9/1983 | Aihara | 422/64 X |
| 4,451,433 | 5/1984 | Yamashita et al. | 422/64 X |
| 4,456,037 | 6/1984 | Gocho | 422/64 X |
| 4,457,893 | 7/1984 | Takekawa | 422/64 |
| 4,459,265 | 7/1984 | Berglund | 422/64 |

Primary Examiner—Alan Cohan
Assistant Examiner—John Rivell
Attorney, Agent, or Firm—Marvin Feldman

[57] ABSTRACT

An automated consecutive reaction analyzer is formed with a rotatable multiple position specimen holder, a specimen transfer arm, and a rotatable multiple positioned specimen reaction holder, with the arm transferring the specimens to the reaction holder and a plurality of reagent holders and dispensers are mounted so as to consecutively dispense the reagents in each specimen reaction holder, and a photometer is operatively positioned to measure the reactions after each consecutive reaction with rotation of the specimen reaction holders. The analyzer is particularly suited for performing consecutive reactions on the same specimen and measuring blood coagulation parameters such as heparin, antithrombin III, plasminogen, plasmin, alpha-2-antiplasmin, plasminogen activator, strepto- and urokinase, Protein C, Factors X and Xa, prothrombin, activated partial thromboplastin time, prekallikrein, alpha-2-macroglobulin, platelet factor 4, trypsin and antitrypsin and any new developing techniques.

7 Claims, 2 Drawing Sheets

AUTOMATED CONSECUTIVE REACTION ANALYZER

FIELD OF THE INVENTION

This invention relates to an apparatus for the analysis of blood or other biological fluids. Specifically, this invention relates to an analyzer for measuring a plurality of consecutive reactions on specimens of blood or other biological fluids.

BACKGROUND AND DISCUSSION OF THE PRIOR ART

With increasing occurrences of open heart surgery, there has arisen the need for faster and more accurate monitoring systems for blood coagulation parameters. Heparin is the anticoagulant of choice for open heart surgery. Generally, during the extracorporeal phase of open heart surgery, heparin is administered in relatively large dosages, to achieve anticoagulation and is then neutralized with protamine, and blood products are supplied. The amount of heparin to be neutralized is currently determined by clotting methods which have been found not to determine heparin quantitatively.

It has been found that neutralization at the peak of extracorporeal circulation is very often not quantitative, with the result that small amounts of heparin remain. It has also been found that at this particular period, the antithrombin heparin cofactor is largely depleted. With the addition of blood products at this point, amounts of heparin may be present and may lead to postoperative bleeding.

The clotting process, particularly in view of these postoperative additions to the blood, provides a complex condition under which it is most desirable to rapidly and accurately determine various postoperative heparin levels.

The art therefore required a device which would rapidly perform accurate measurements of coagulation parameters on blood specimens involving consecutive reactions by using a large number of reagents.

Various attempts have been made to provide automatic blood and biological fluid analyzers, such as is disclosed in U.S. Pat. No. 3,488,156, issued Jan. 6, 1970 to Good et al.; U.S. Pat. No. 3,489,525, issued Jan. 13, 1970 to Natelson; U.S. Pat. No. 3,634,868, issued Jan. 11, 1972 to Pelavin et al.; U.S. Pat. No. 3,941,479, issued Mar. 2, 1976 to Whitehead; U.S. Pat. No. 4,030,888, issued June 21, 1977 to Yamamoto et al.; U.S. Pat. No. 4,063,309, issued Dec. 13, 1977 to Hennessy et al. and U.S. Pat. No. 4,134,678, issued Jan. 16, 1979 to Brown et al. One other prior art automated chemical diagnostic analyzer is the ATAC 3000, manufactured by Turpen Laboratories Systems, Inc., Jackson, N.J.

These prior art attempts did not provide the multiple consecutive analysis of multiple specimens in a rapid and yet accurate manner, so as to advise the physician in the operating room of certain crucial parameters, such as the blood coagulation parameters. The aforesaid prior art devices were generally limited to two sequential reactions at most.

SUMMARY OF THE INVENTION

An automated consecutive multiple analyzer combines a rotatable multiple position specimen holder, a pivotally mounted specimen transfer arm and syringe, and a rotatable multiple positioned specimen reaction holder which includes a plurality of reagent holders and dispensers for each of the reagents, with photometers operatively mounted to the reaction holders, and with automated programmed controls for cooperative operation of these elements, so that a specimen is transferred by the transfer arm syringe from the specimen holder to a reaction holder whereat a first reagent is added to cause a first reaction and photometric measurement thereof, and a second reagent is subsequently added to cause a second reaction with a second photometric measurement and continued consecutive reaction if desired.

The invention sets forth a specific arrangement and combination of the aforesaid elements which provide multiple consecutive reactions for several different patients to be conducted simultaneously, or numerous multiple sequential reactions for one patient on a practical operating room location analyzer.

DESCRIPTION OF THE PREFERRED EMBODIMENTS

In one aspect the present invention is an automated consecutive reaction analyzer having a first member being formed with specimen holding means for holding a plurality of specimen holders and means to move said specimen holding means; a second member being formed with reaction holding means for holding a plurality of holders containing specimens undergoing reaction and means to move said specimen reaction holding means, the second member further comprising first and second reagent holding means for separately holding a plurality of holders containing first and second reagents; first arm means being movably mounted between the members for transferring a specimen from the specimen holder to the specimen reaction holder; and second arm means operatively disposed on said second member to transfer a first reagent from the first reagent holder to the one said transferred specimen reaction holder, and then to transfer a second reagent to one said reaction holder to consecutively cause a first reaction and then a second reaction; with measuring means being mounted adjacent the reaction holders so as to determine a reaction parameter of the transferred specimen after the first reaction and then after the second reaction with movement of the second member to bring the reaction holder adjacent the reaction measuring means; and control means being interconnected respectively to the first member, second member, first arm means and second arm means for cooperative movement thereof, whereby consecutive reactions are effected and automatically measured.

Figure 1:
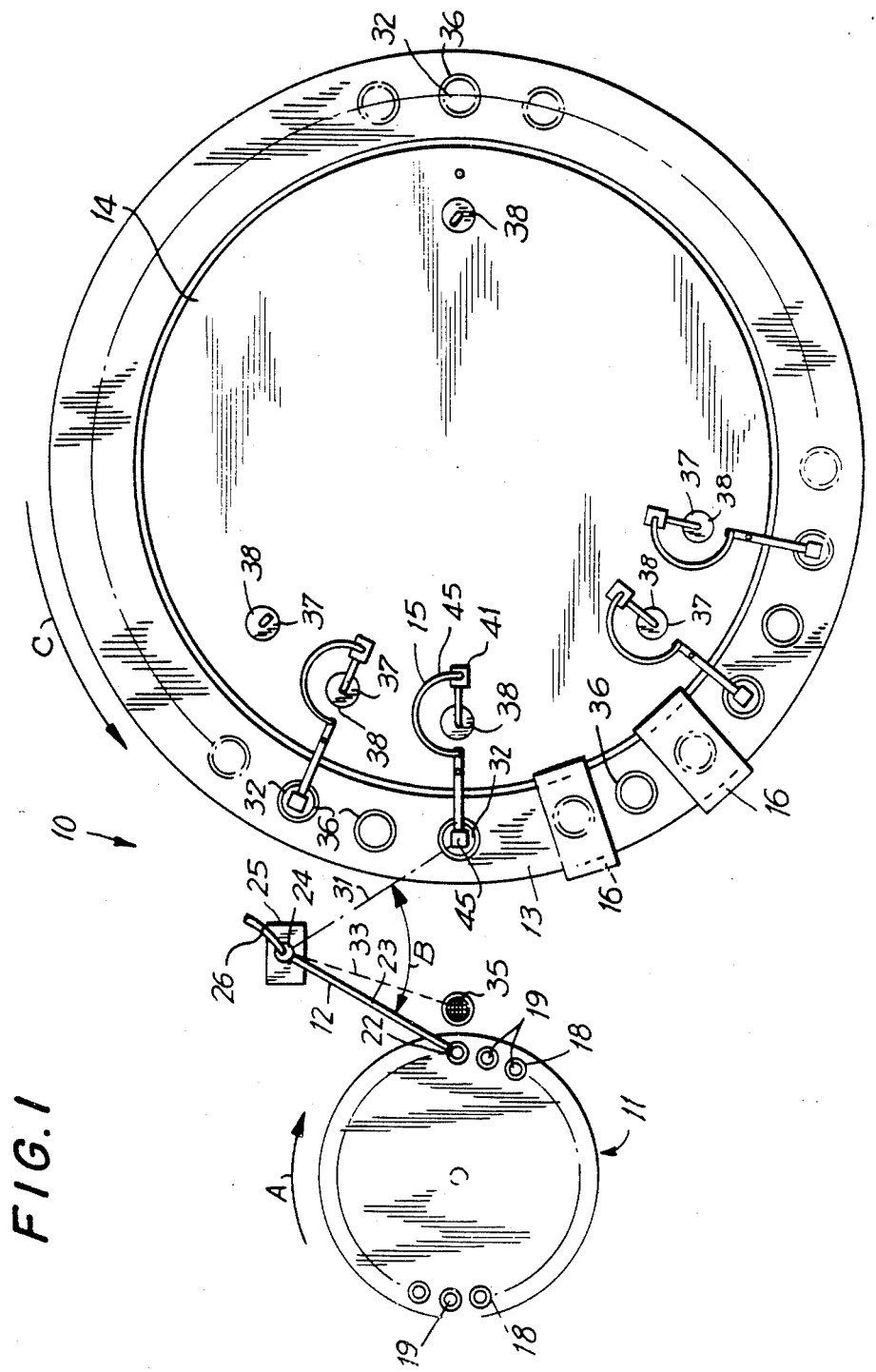
FIG. 1 is a plan partial schematic view of the analyzer of the present invention.
Figure 2:
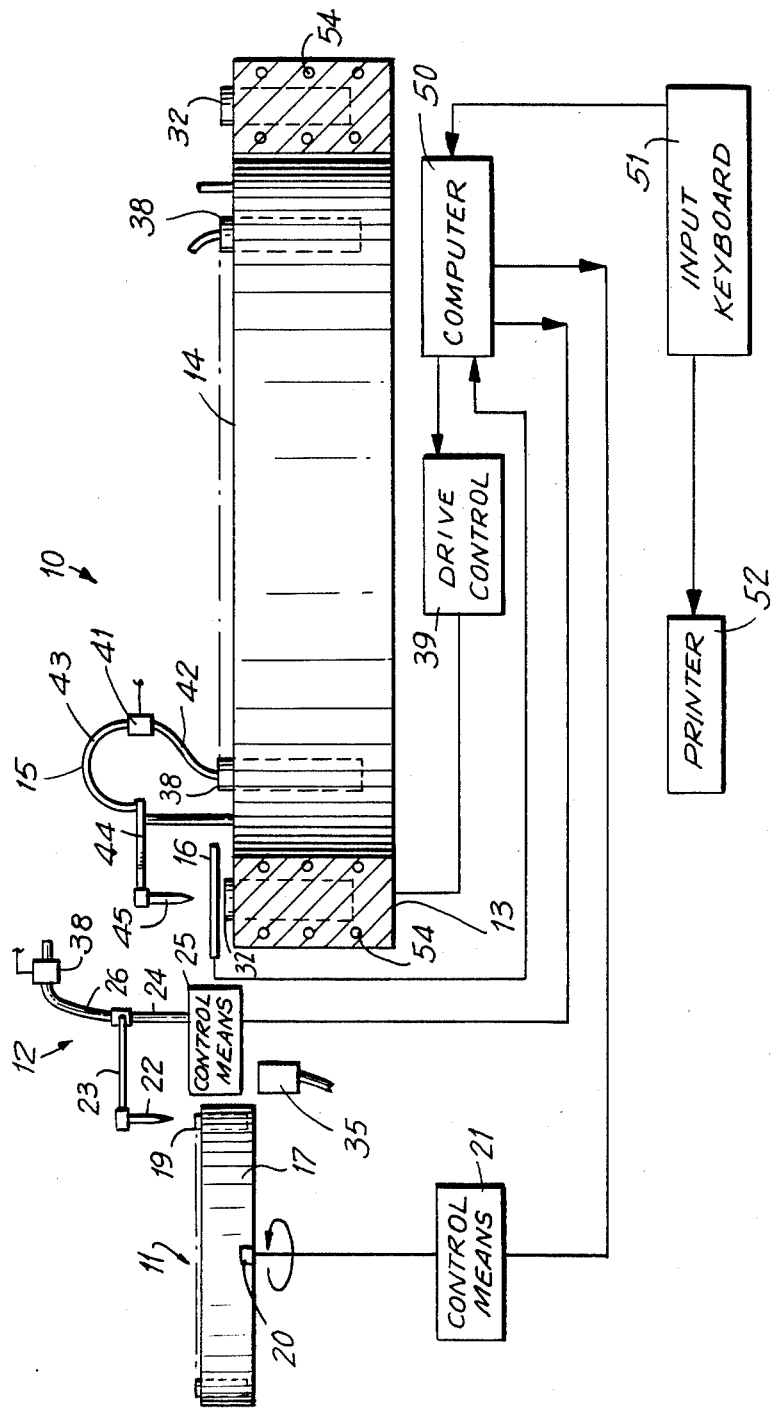
FIG. 2 is a sectional partial schematic view taken along line 2—2 of FIG. 1.

Referring now to FIGS. 1 and 2, there is shown the analyzer of the present invention generally referred to as 10. Analyzer 10 in general includes a rotatable multiple position specimen holder 11, a pivotable specimen transfer arm 12, a rotatable multiple position annular-shaped specimen reaction holder 13, a central fixed reagent holder unit 14, reagent transfer arms 15 (typical) and two radially spaced photometers 16 disposed along reaction holder 13.

Specimen holder 11 is formed of a cylindrical body 17, having a plurality of circumferentially spaced recesses 18 for receiving a plurality of specimen holders or cuvets 19. Rotation elements 20 and indexing control means 21 are integrally operationally connected to the holder 11 by well known means for controlled indexing of holder 11 for reasons hereinafter appearing. Holder 11 rotates in the direction shown by arrow A.

Specimen transfer arm 12 is formed of a vertically downwardly disposed syringe 22 integrally connected to fluid conduit horizontal arm 23 which in turn is connected to reversibly rotatable vertical vacuum control support arm 24 with control means 25 and flush fluid supply hose 26. Arm 12 is reversibly rotatable between specimen holder 11 and reaction holder 13 as shown by arrow B. Syringe 22 operates by the drawing of vacuum by conventional means (not shown), through arms 24 and 23 so as to suck up a specimen sample from cuvet 19. Control means 25 then causes the rotation of arm 12 to position 31, whereat the release of the vacuum causes deposition of the specimen into reaction cuvet 32 of reaction holder 13. After deposition of the specimen, arm 12 is reversibly pivoted to a position 33 where a flush liquid (e.g., water) is passed from hose 26 through arm 23 and syringe 22 to to flush residual specimen into flush receptacle 35. Control means 38 controls the flush fluid flow to arm 12. Arm 12 is then pivoted back to its original position at specimen holder 11. During the afore-described action of arm 12, holder 11 is indexed to place a second specimen cuvet in position for second specimen removal by syringe 22 and transfer by arm 12.

Referring now specifically to reaction holder 13 and reagent holder 14, there is shown a plurality of circumferentially equally spaced recesses 36 for receiving reaction cuvets 32, and a plurality of circumferentially equally spaced recesses 37 for receiving reagent supply containers 38. Reaction holder 13 is rotatably (arrow C) indexed by drive control 39, so that in each indexing, a reaction cuvet 32 is immediately adjacent a reagent container 38. A reagent supply or transfer arm unit 15 is disposed between each set of adjacent cuvets 37 and containers 38. Fluid control means 41 interconnects reagent conduits 42, 43 and 44 through syringe 45 for the controlled volume flow of the specific reagent to the reaction cuvet 32. With the transfer of a controlled amount of reagent to the specimen in the reaction cuvet, a reaction occurs under temperature controlled conditions by temperature control elements 54, and with indexing of the cuvet to a photometer position, one or more reaction parameters are measured in the conventional manner. Control means 41, as well as the other aforesaid control means are interconnected to computer 50, for coordinated control of the system.

Programming, data storage and control of the automated sequential reaction analyzer may readily be effected with a Hewlett Packard HP85A or HP85B computer with an RS232 interface. The readily adapted program is stored on tape and automatically fed to this computer. An input keyboard 51 and printer 52 of conventional design completes the system.

It is important to note that multiple consecutive reactions may be effected and photometer readings may be taken for each specimen. The number and types of reagents may be greatly varied as well as the time and sequencing of the cuvets with the photometers.

What is claimed is:

1. An automated consecutive reaction analyzer comprising a first member being formed with specimen holding means for holding a plurality of specimen holders and means to move said specimen holding means;

a second member being formed with specimen reaction holding means for holding a plurality of specimen reaction holders containing specimens undergoing reaction and means to move said specimen reaction holding means, said second member further comprising first and second reagent holding means comprising holders respectively containing first and second reagents, said reaction holding means being movable relative to the reagent holding means so that each reaction holder is operatively adjacently positioned to each reagent holder;

first arm means being movably mounted between the members for transferring a specimen from one said specimen holder to one said specimen reaction holder;

second arm means operatively disposed on said second member to transfer the first reagent from the respective reagent holder to the one said transferred specimen reaction holder, and to transfer a second reagent to the one said reaction holder to consecutively cause a first reaction and then a second reaction, said second arm means comprising a plurality of reagent dispensing arms respectively mounted at each reagent holder for dispensing one of the specific respective reagents to the immediately adjacent reaction holder;

measuring means being mounted adjacent said reaction holder so as to measure a reaction parameter of the transferred specimen after initiation of said first reaction and then after initiation of said second reaction with movement of said second member to bring the one said reaction holder adjacent said reaction measuring means; and control means being inter-connected respectively to said first member, second member, first arm means and second are means for cooperative movement thereof, said reaction measuring means comprising two circumferentially spaced photometers, so that one reaction holder is operatively disposed adjacent one photometer, and another said reaction holder is operatively disposed adjacent the other photometer, said plurality of reagent dispensing arms comprising a first plurality and a second plurality, said first plurality being positioned upstream of the movement direction of the reaction holding means and circumferentially spaced from said first photometer and adjacent said first arm means, and said second plurality being positioned downstream of the movement direction of the reaction holding means and circumferentially spaced from said second photometer and more remote from said first arm means than said first plurality, whereby a first reagent is added to a reaction holder to cause of first reaction and photometric measurement thereof, and a second reagent is subsequently added to a reaction holder cause a second reaction and photometric measurement thereof, said first member specimen holders being circumferentially disposed on said first memer, said second member comprising first and second cylinders, said cylinders being coaxial and said reaction holders being circumferentially disposed and radially spaced from the reagent holders, whereby said consecutive reactions are effected and automatically measured.

2. The analyzer of claim 1, further comprising a third reagent holder containing a third reagent, said second arm means being operatively connected between the third reagent holder and the one said specimen reaction holder to effect a third consecutive reaction.

3. The analyzer of claim 1, said first arm means being pivotally connected so as to be reversibly pivoted between said first member and said second member.

4. The analyzer of claim 3, said first arm means comprising means to flush the first arm means.

5. The analyzer of claim 1, said specimen and reagent holders being cuvets.

6. The analyzer of claim 5, said first arm means comprising a syringe.

7. The analyzer of claim 6, each said second arm means comprising a syringe.

* * * * *